US009446246B2

(12) United States Patent
Schecter et al.

(10) Patent No.: US 9,446,246 B2
(45) Date of Patent: Sep. 20, 2016

(54) IDENTIFICATION OF ELECTRO-MECHANICAL DYSYNCHRONY WITH A NON-CARDIAC RESYNCHRONIZATION THERAPEUTIC DEVICE

(75) Inventors: Stuart O. Schecter, Great Neck, NY (US); Xiaoyi Min, Thousand Oaks, CA (US)

(73) Assignee: PACESETTER, INC., Sylmar, CA (US)

(*) Notice: Subject to any disclaimer, the term of this patent is extended or adjusted under 35 U.S.C. 154(b) by 2107 days.

(21) Appl. No.: 12/267,376

(22) Filed: Nov. 7, 2008

(65) Prior Publication Data

US 2010/0121403 A1    May 13, 2010

(51) Int. Cl.
| | |
|---|---|
| *A61N 1/368* | (2006.01) |
| *A61B 5/053* | (2006.01) |
| *A61N 1/00* | (2006.01) |
| *A61N 1/365* | (2006.01) |
| *A61N 1/362* | (2006.01) |

(Continued)

(52) U.S. Cl.
CPC ............ *A61N 1/368* (2013.01); *A61B 5/0538* (2013.01); *A61N 1/3627* (2013.01); *A61B 5/0452* (2013.01); *A61N 1/3684* (2013.01); *A61N 1/36521* (2013.01); *A61N 1/3702* (2013.01)

(58) Field of Classification Search
CPC ............ A61N 1/368; A61N 1/36521; A61N 1/36527; A61B 5/0538
USPC ..................................... 607/4, 14, 17, 27–28
See application file for complete search history.

(56) References Cited

U.S. PATENT DOCUMENTS

| 4,947,854 A | 8/1990 | Rabinovitz et al. |
| 5,139,020 A | 8/1992 | Koestner et al. |
| 5,156,154 A | 10/1992 | Valenta, Jr. et al. |

(Continued)

FOREIGN PATENT DOCUMENTS

| EP | 0503839 A2 | 9/1992 |
| WO | 0069490 | 11/2000 |

(Continued)

OTHER PUBLICATIONS

Borges, A.C. et al., "Echocardiographic evaluation to select patients for cardiac resynchronization therapy," Herzchr Elektrophys. 2006;17(Supp. 1):1/63-1/72.

(Continued)

*Primary Examiner* — Catherine Voorhees

(57) ABSTRACT

An implantable cardiac therapy device and methods of using a device including an implantable stimulation pulse generator, one or more implantable leads defining sensing and stimulation circuits adapted to sense and deliver therapy in at least one right side heart chamber, and an implantable controller in communication with the stimulation pulse generator and the one or more patient leads so as to receive sensed signals indicative of a patient's physiologic activity and deliver indicated therapy. The controller is adapted to monitor at least one indicator of cardiac dysynchrony and to compare the at least one indicator to a determined dysynchrony threshold. The threshold is determined for indications that the patient be further evaluated for cardiac resynchronization therapy. The controller is further adapted to set an alert when the at least one indicator exceeds the threshold to indicate to a clinician that evaluation for bi-ventricular pacing might be indicated.

7 Claims, 5 Drawing Sheets

(51) Int. Cl.
*A61B 5/0452* (2006.01)
*A61N 1/37* (2006.01)

(56) References Cited

U.S. PATENT DOCUMENTS

| | | | |
|---|---|---|---|
| 5,188,106 | A | 2/1993 | Nappholz et al. |
| 5,544,656 | A | 8/1996 | Pitsillides et al. |
| 6,522,923 | B1 | 2/2003 | Turcott |
| 6,540,699 | B1 | 4/2003 | Smith |
| 6,760,615 | B2 | 7/2004 | Ferek-Petric |
| 6,766,189 | B2 | 7/2004 | Yu et al. |
| 6,792,310 | B1 | 9/2004 | Turcott et al. |
| 6,923,772 | B2 | 8/2005 | Yu et al. |
| 6,993,389 | B2 | 1/2006 | Ding et al. |
| 7,041,061 | B2 | 5/2006 | Kramer et al. |
| 7,203,542 | B2 * | 4/2007 | Obel ............... 607/27 |
| 2002/0143264 | A1 | 10/2002 | Ding et al. |
| 2002/0161307 | A1 | 10/2002 | Yu et al. |
| 2003/0083586 | A1 | 5/2003 | Ferek-Petric |
| 2004/0044374 | A1 * | 3/2004 | Weinberg et al. ............ 607/25 |
| 2004/0049112 | A1 | 3/2004 | Yu et al. |
| 2004/0122479 | A1 | 6/2004 | Spinelli et al. |
| 2004/0162496 | A1 | 8/2004 | Yu et al. |
| 2004/0220637 | A1 | 11/2004 | Zdeblick et al. |
| 2005/0027323 | A1 | 2/2005 | Mulligan et al. |
| 2005/0107839 | A1 | 5/2005 | Sanders |
| 2005/0131469 | A1 | 6/2005 | Cohen |
| 2005/0182447 | A1 * | 8/2005 | Schecter ............ 607/2 |
| 2005/0203579 | A1 | 9/2005 | Sowelam et al. |
| 2005/0288727 | A1 | 12/2005 | Penner |
| 2006/0167529 | A1 * | 7/2006 | Schecter ............ 607/59 |
| 2007/0249945 | A1 * | 10/2007 | Li et al. ............ 600/515 |
| 2008/0114256 | A1 * | 5/2008 | Zhang et al. ............ 600/488 |

FOREIGN PATENT DOCUMENTS

| | | |
|---|---|---|
| WO | 2004067081 A2 | 8/2004 |
| WO | 2004067081 A3 | 8/2004 |
| WO | 200507075 A3 | 1/2005 |
| WO | 2005007075 A2 | 1/2005 |
| WO | 2005018570 A2 | 3/2005 |
| WO | 2005018570 A3 | 3/2005 |
| WO | 2005020025 A2 | 3/2005 |
| WO | 2005020025 A3 | 3/2005 |

OTHER PUBLICATIONS

Koglek, W. et al., "Three dimensional vectorcardiography to predict CRT-responder," Herzchr Elektrophys. 2006;17(Supp. 1):1/28-1/36.

* cited by examiner

IDENTIFICATION OF ELECTRO-MECHANICAL DYSYNCHRONY WITH A NON-CARDIAC RESYNCHRONIZATION THERAPEUTIC DEVICE

BACKGROUND OF THE INVENTION

1. Field of the Invention

The invention relates to the field of implantable cardiac stimulation devices and to identifying patients exhibiting electro-mechanical dysynchrony.

2. Description of the Related Art

Numerous patients suffer from disease conditions that affect their cardiac performance. For example, diseased myocardium generally reduces the mechanical contractile capabilities of the heart. Impaired conduction and/or abnormalities in intrinsic activation can result in inappropriate/impaired stimulation of the cardiac tissue. Damaged valves can limit the sealing capabilities of the heart thereby reducing capacity for normal filling and/or emptying. Dysynchrony in activity among the multiple cardiac chambers also impairs pumping effectiveness.

A variety of implantable cardiac stimulation devices have been developed to provide therapy for at least certain patients suffering impaired cardiac function. Implantable cardiac stimulation devices generally include an implantable stimulation pulse generator and a microprocessor based controller regulating operation of the device. Implantable cardiac stimulation devices also typically include one or more implantable leads which are configured for implantation to extend adjacent the patient's heart. The implantable leads typically include one or more electrodes. The electrodes can be configured for dedicated sensing or for delivery of stimulation or can be configured for combined sensing and stimulation delivery functions. The implantable devices are generally adapted to automatically sense the patient's physiologic status and automatically generate and deliver therapeutic stimulation for observed cardiac abnormalities.

The implantable devices available range in complexity and modes of therapy delivery, for example the particular chamber(s) of the heart which receive therapeutic stimulation. An appropriate configuration and programming of the device is selected depending on clinical evaluations of the individual needs of the patient. Thus, an implantable cardiac stimulation device and corresponding implantable sensing/stimulation lead(s) are configured and operation is programmed for the individual needs of each patient and their individual conditions.

For example, bradycardia pacing devices are adapted to provide therapeutic pacing stimulation to counteract slow arrhythmias. Implantable cardioverter/defibrillators (ICDs) are adapted to provide therapy for tachycardia/fibrillation arrhythmias. Implantable devices can also be configured to provide anti-tachycardia pacing therapy to overdrive pace the heart to treat certain tachycardias.

Multi-chamber pacing can offer significant benefits to certain arrhythmic patients. Bi-ventricular (or Bi-V) pacing is one particular variation of multi-chamber pacing that refers to pacing both the right and left ventricles as indicated. By providing paced control of both ventricles, bi-ventricular pacing can help restore synchrony between the ventricles and increase the overall pumping efficiency of the heart. Such therapy is also frequently referred to as cardiac resynchronization therapy (CRT) as such therapy can be adapted to improve right-left synchronization of ventricular activity.

Multi-chamber pacing is one of the more complicated and expensive therapies available via implantable cardiac stimulation devices. In the particular example of bi-ventricular pacing, as the left ventricle (LV) provides the most energetic contractions of the heart chambers and placing foreign objects inside the LV presents serious risks, implanting stimulation leads into effective contact with the left ventricle is a challenging procedure both for the designers of the implantable device and the physician performing the implantation. Thus, bi-ventricular pacing, while offering significant benefits to certain patients, is also relatively expensive to implement and involves a more complicated and potentially more risky implantation procedure than other implantable device configurations. It will be appreciated that this more complex and expensive therapy is generally reserved for patients for whom a clear potential benefit can be demonstrated.

However, at least certain patients who are not provided with a bi-ventricular-capable device, for example patients provided with a bradycardia pacer or an ICD, may experience a change in their condition such that they may benefit from the more complex bi-ventricular-capable device. For example, at least certain patients provided with bradycardia pacing can be at risk for developing dysynchrony and deleterious remodeling from RV pacing. Patients provided with ICDs often have cardiomyopathy and/or heart failure (HF). Such patients may exhibit a worsening in their condition such that a Bi-V capable or CRT device may become indicated when it previously was not.

Ultrasound imaging can provide information to assist a physician in evaluating potential dysynchrony conditions, however, use of ultrasound techniques is not universally well understood or available. Electrogram measures, for example QRS width, can also be used as indicators of dysynchrony, however do not provide accurate results in at least certain cases. It will be understood that there is a need for improved systems and methods for identifying onset or worsening dysynchrony conditions, especially in patients who have not previously exhibited significant dysynchronous conditions. It would be further advantageous to provide systems and methods of identifying onset or worsening dysynchrony conditions without requiring additional equipment or clinical diagnostics to increase convenience to the patient and attending clinician while maintaining availability of the improved diagnosis to a wider patient population.

SUMMARY OF THE INVENTION

Certain embodiments are based at least partially on an understanding that existing means for identifying patients exhibiting cardiac dysynchrony that may benefit from a biventricular pacing capable device but are not currently provided with one suffer limitations. For example, while measured QRS width has been used as an indicator of dysynchrony, in at least certain applications QRS width lacks sufficient specificity or sensitivity to accurately determine dysynchrony. Embodiments are also based at least partially on an understanding that electrical intra-ventricular conduction abnormalities can exist in patients with otherwise substantially normally QRS widths. Mechanical delays in cardiac deformation/motion can also exist which are not easily detected with at least certain known diagnostic techniques.

Certain embodiments employ an implantable device that is capable of long-term extended monitoring of the patient's physiologic condition to define activation patterns that are not easily identifiable on at least certain diagnostic instruments, for example, surface ECGs. Certain embodiments facilitate identifying dysynchrony in a patient provided with a non Bi-V capable or CRT capable pacing system via the implantable device. Certain embodiments include evaluation of data such as frequent single right ventricular chamber pacing, timing data obtained from intracardiac electrograms and/or impedance based measurements to facilitate identification of dysynchrony, particularly in patients newly exhibiting such conditions.

One embodiment includes an implantable cardiac therapy device, the device comprising an implantable stimulation pulse generator, one or more implantable patient leads defining sensing and stimulation circuits adapted to sense and deliver therapy in at least one right side heart chamber, and an implantable controller in communication with the stimulation pulse generator and the one or more patient leads so as to receive sensed signals indicative of a patient's physiologic activity, the controller being adapted to evaluate the patient's physiologic activity as indicated by the received sensed signals and to induce the stimulation pulse generator to deliver therapeutic stimulation via the one or more patient leads and wherein the controller is further adapted to monitor at least one indicator of cardiac dysynchrony and to compare the at least one indicator to a determined dysynchrony threshold wherein the threshold is determined for indications that the patient be further evaluated for cardiac resynchronization therapy and wherein the controller is further adapted to set an alert when the at least one indicator exceeds the threshold.

Another embodiment includes a method of evaluating a patient's condition via an implantable cardiac therapy device, the method comprising implanting and programming an implantable cardiac therapy device so as to provide therapy of a first configuration, defining a dysynchrony threshold, storing the dysynchrony threshold in the implantable cardiac therapy device, internally sensing a patient's physiologic activity with the implantable cardiac therapy device, evaluating the sensed physiologic activity with the implantable cardiac therapy device, determining a dysynchrony index, comparing the dysynchrony index to the dysynchrony threshold, and setting an alert with the implantable cardiac therapy device when the dysynchrony index exceeds the dysynchrony threshold, the alert indicating that the patient may benefit for being provided with therapy of a second configuration. These and other objects and advantages of the invention will become more apparent from the following description taken in conjunction with the accompanying drawings.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
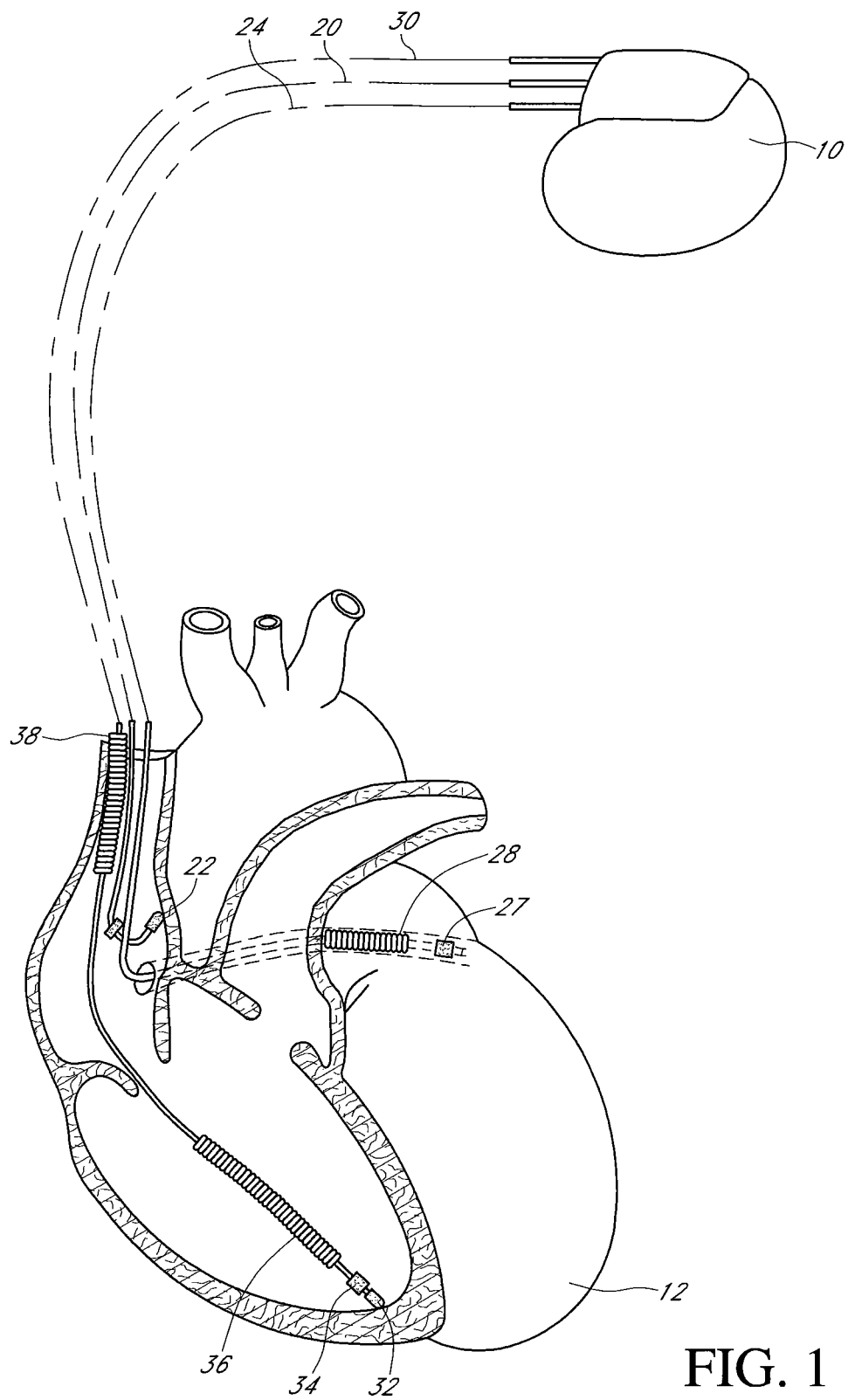
FIG. 1 is a simplified diagram illustrating a therapeutic appliance with an implantable stimulation device in electrical communication with at least one lead implanted into a patient's heart for delivering stimulation therapy.

FIG. 1 illustrates one embodiment of an implantable cardiac stimulation device 10 in electrical communication with a patient's heart 12 byway of one or more of three leads, 20, 24 and 30, suitable for delivering single or multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial cardiac signals and to provide left chamber pacing therapy, the stimulation device 10 is coupled to a "coronary sinus" lead 24 designed for placement in the "coronary sinus region" via the coronary sinus ostium (OS) for positioning one or more electrodes adjacent to the left atrium. Accordingly, an exemplary coronary sinus lead 24 is designed to receive atrial cardiac signals and to deliver left atrial pacing therapy using at least a left atrial ring electrode 27 and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
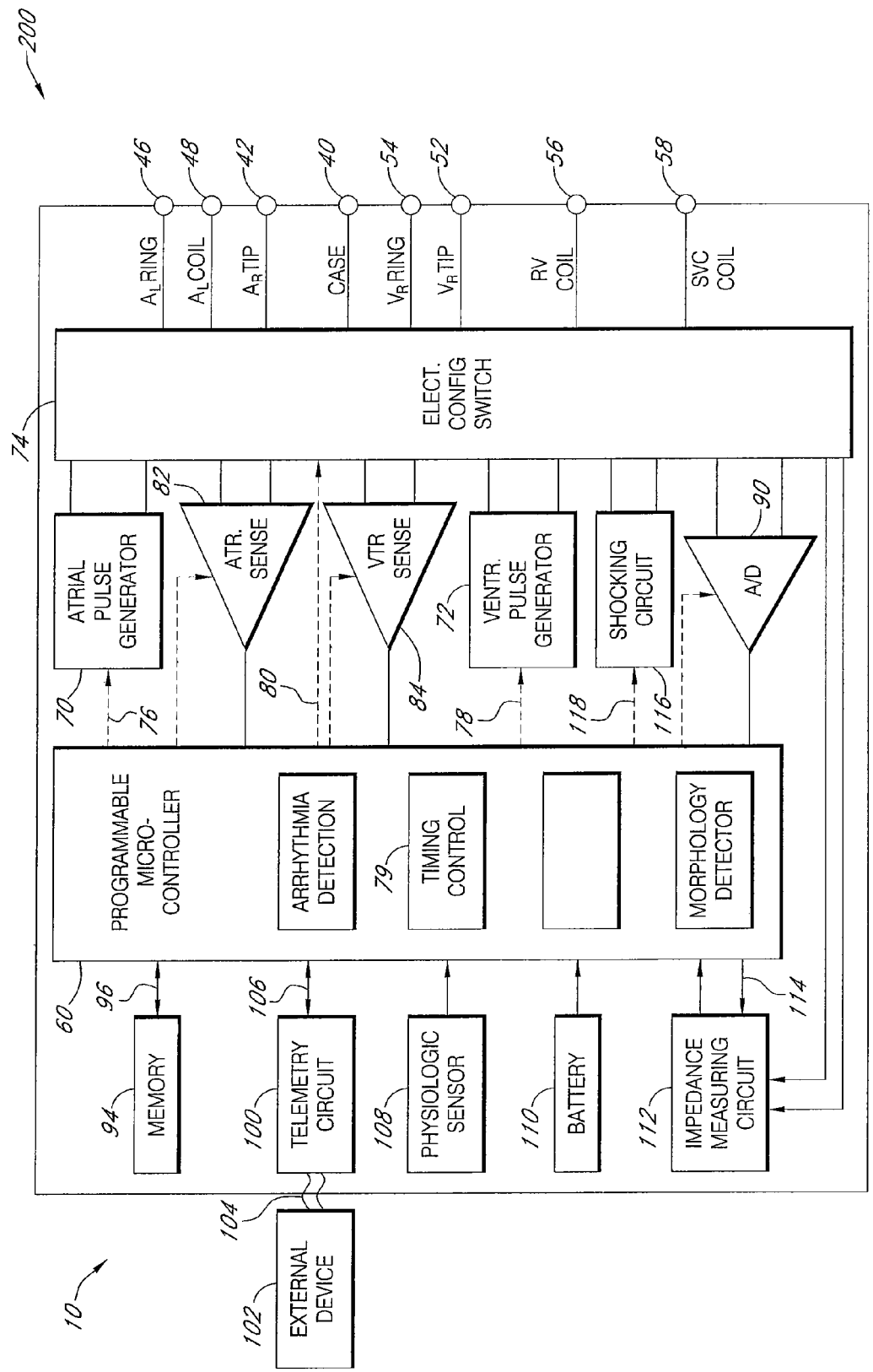
FIG. 2 is a functional block diagram of a multi-chamber implantable stimulation device illustrating elements of a stimulation device that can provide cardioversion, defibrillation and pacing stimulation in one or more chambers of the heart.

As illustrated in FIG. 2, a simplified functional block diagram is shown of the single or multi-chamber capable implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and/or pacing stimulation as indicated for the particular application.

The housing 40 for the stimulation device 10, shown schematically in FIG. 2, is often referred to as the "can", "case" or "case electrode" and may be programmably selected to act as the return electrode for all pacemaker "unipolar" modes. The housing 40 may further be used as a return electrode alone or in combination with one or more of the coil electrodes 28, 36 and 38, for shocking purposes. The housing 40 further includes a connector having a plurality of terminals, 42, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left atrial sensing, pacing and shocking, the connector includes at least a left atrial ring terminal ($A_L$ RING) 46 and a left atrial shocking terminal ($A_L$ COIL) 48, which are adapted for connection to the left atrial ring electrode 27 and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy to the atria and/or right ventricle, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (A V) delay, atrial interconduction (A-A) delay as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high-resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart as described in greater detail below.

Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, timing/delays and the amplitude, wave shape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In certain preferred embodiments, the stimulation device 10 further includes a physiologic sensor 108, commonly referred to as a "rate-responsive" sensor because it can be used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, etc.) at which the atrial and ventricular pulse generators, 70 and 72, generate stimulation pulses.

The stimulation device additionally includes a battery 110 that provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monofluoride or a hybrid of the two.

As further shown in FIG. 2, the device 10 is shown as having an impedance measuring circuit 112 that is enabled by the microcontroller 60 via a control signal 114. The impedance measuring circuit 112 is adapted to provide a known current or voltage, measure a resulting voltage or current, and thereby determine an impedance of the interposed materials. In one embodiment, the circuit 112 is adapted to deliver pulses of approximately 200 µA and 30 µS width at a frequency of 128 Hz. Such pulses generally will not depolarize myocardium, cause limited battery drain, and operate at a frequency that acts as a band pass filter to improve signal to noise ratio of the sensed impedance. In certain implementations, it is preferred that the amplitude, pulse width, and frequency of current stimulation of the circuit 112 be variable for optimization for various applications. In certain embodiments, the impedance measuring circuit 112 preferably supports determinations of multiple impedance measurements, for example along multiple spatially arranged sensing vectors.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses can be applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As previously noted, embodiments can comprise any of a number of combinations and sub-sets of the functionalities and components of the device 10 as previously described and do not require all of the capabilities and components described.

Figure 3:
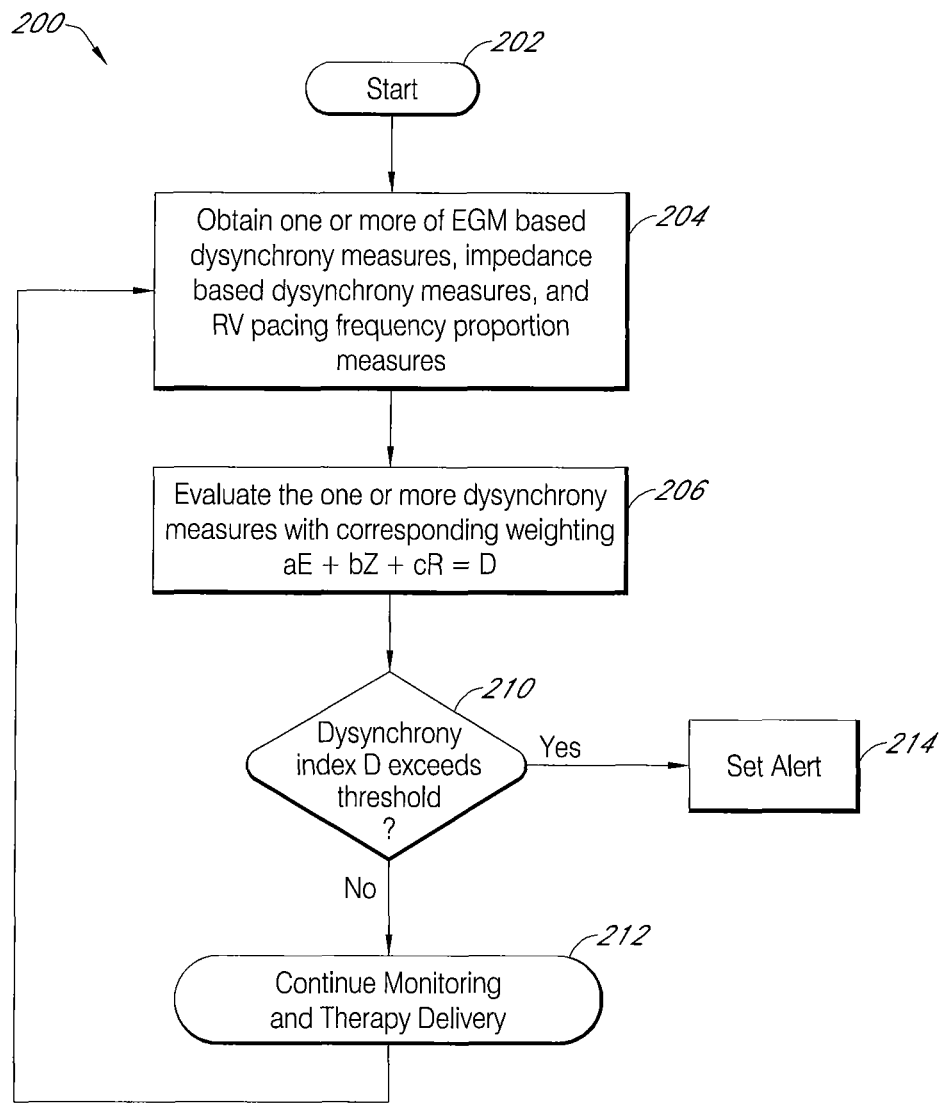
FIG. 3 is a flow chart of embodiments of a system and method of identifying electro-mechanical dysynchrony with a non-cardiac resynchronization configured implantable therapy device.

FIG. 3 is a flow chart illustrating embodiments of a system and method 200 of identifying electromechanical dysynchrony with a non-cardiac resynchronization therapeutic device. The method 200 begins in a start state 202 which can include implantation and programming of an appropriate configuration of the device 10 as previously described for the particular needs of a given patient. As previously noted, in at least certain applications, the patients condition and therapeutic needs can change over time, however, the start block 202 generally assumes that the patient is provided with a configuration and programming of the device 10 that is at least initially not configured for delivery of cardiac resynchronization therapy.

Following from the start block 202 is a measurement block 204 wherein one or more measures of potential dysynchrony are obtained at least partially by the device 10. These measures can include one or more of an electrogram-based measure of dysynchrony, an impedance measurement-based dysynchrony measure and/or a measure indicative of the frequency or proportion of pacing therapy that has been delivered to the right ventricle.

Electrogram measurements are indicative of the electrical activity of the heart 12, for example indicative of cyclical depolarizations and repolarizations. Impedance measurements are indicative of mechanical activity of the heart as impedance of regions of cardiac tissue changes over time with contraction and relaxation of the myocardium. In addition, impedance measurements across regions of the heart change over time as relatively high conductivity blood enters and exits the heart chambers. High resolution impedance measurements can provide signals indicative of valvular activity. The frequency of RV pacing and/or the proportion of RV pacing occurring can be clinically relevant indicators for Bi-V pacing.

Following from the measurement block 204, is an evaluation block 206, wherein the one or more measures of potential dysynchrony obtained in block 204 are evaluated.

In at least certain embodiments, weighting factors can be applied to one or more of the potential dysynchrony measures obtained in block 204. For example, in a given application, indications of dysynchrony based on EGM measurements can be weighted differently than the frequency of RV pacing. These concepts are illustrated generally by the formula aE+bZ+cR=D where aE represents EGM-based dysynchrony measures with weighting factor a, bZ represents impedance-based dysynchrony measures with weighting b, cR indicates RV pacing frequency with weighting factor c and D corresponds to a resulting dysynchrony index.

Following from the block 206, the dysynchrony index D is compared to a threshold in a decision block 210. If the result of the decision block 210 is negative, e.g., that the dysynchrony index D does not exceed a determined threshold, the system and method 200 proceed to a block 212 wherein the previously programmed monitoring and therapy delivery of the device 10 proceeds. In certain embodiments, the blocks 204, 206, and 210 can be reiterated after a delay interval and/or when triggered by an event such as receipt of a command from the external device 102.

If the result of block 210 is affirmative, e.g., that the dysynchrony index does exceed the determined threshold, a block 214 follows wherein an alarm is set to indicate the elevated dysynchrony index D. In certain embodiments, the alert of block 214 can comprise setting a flag internally in the device 10 that can be accessed, for example, via a telemetric link 104 with an external device 102. In other embodiments, the alert of block 214 can comprise an audible or otherwise tactile alert generated for delivery to the patient to notify them of the need to contact their physician for further follow-up. In yet other embodiments, the alert of block 214 can comprise an active communication by the device 10, such as via the telemetric link 104 with an external communication network to provide the alert information to the patient's physician. Following from the alert of block 214, the system and method 200 would proceed to the block 212 for further monitoring of the patient and delivery of indicated therapy.

Figure 4:
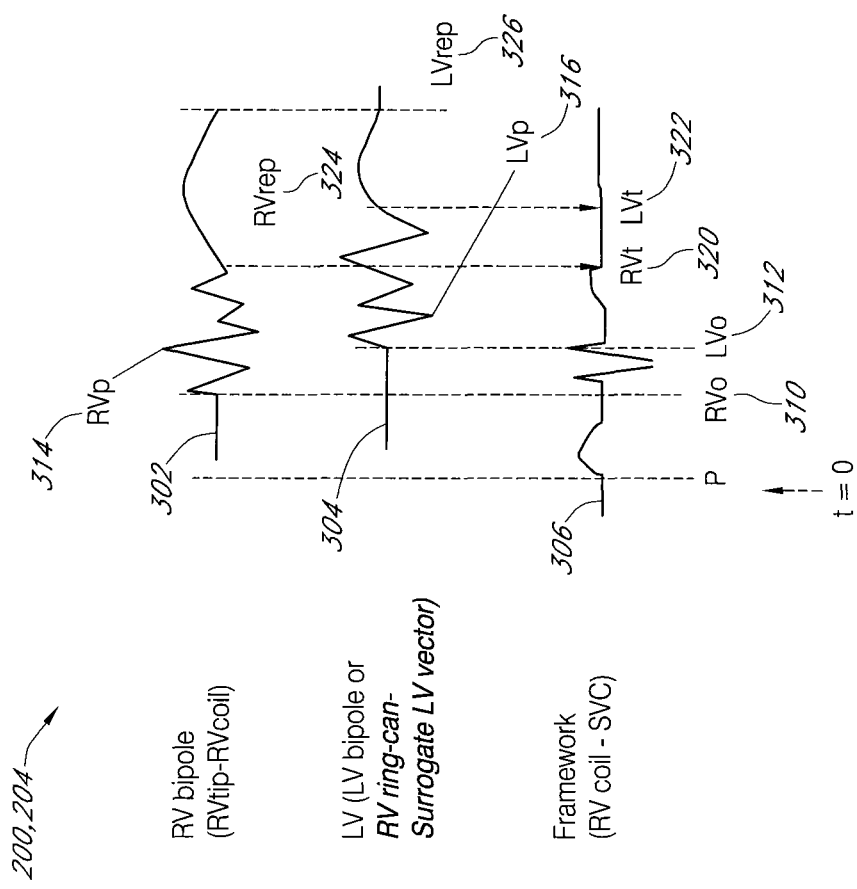
FIG. 4 illustrates exemplary electrogram waveforms indicative of physiologic activity as measured along different sensing vectors.

FIG. 4 illustrates further embodiments of the system and method 200 and the measurement of block 204. As previously noted, the device 10 is adapted to internally monitor electrical activity related to the patient's cardiac activity to generate one or more EGM signals. As illustrated in FIG. 4, in one embodiment this comprises a first EGM waveform 302 corresponding generally to an RV bipole, for example, as measured between an RV tip and an RV coil electrode. This embodiment also comprises a second waveform 304 corresponding, for example, to measurements performed between an RV ring and a can electrode. The second EGM waveform 304 can be considered as an LV bipole or surrogate LV vector.

As previously noted, various embodiments are directed at least partially to identification of patients who are exhibiting an elevated degree of dysynchrony and may benefit from CRT therapy, however, who have not yet been provided with a CRT capable device 10. Thus, the second EGM waveform 304 provides the advantage of providing signals indicative of left ventricular activity in applications where dedicated LV sensing has not yet been implemented. This embodiment also comprises a third EGM waveform 306 obtained, for example, between an RV coil and SVC electrodes which can be considered to provide a framework waveform.

As illustrated in FIG. 4, the EGM waveforms 302, 304, and 306 define a plurality of fiducial points or monuments that can be evaluated as indicators of relative synchrony dysynchrony. For example, the first waveform 302 defines a fiducial point corresponding to the onset of RV depolarization indicated as RVo 310. Similarly, the second waveform 304 defines a monument corresponding to the onset of LV depolarization indicated LVo 312. The first and second waveforms 302, 304 also define peaks of RV and LV depolarization indicated as RVp 310 and LVp 316, respectively.

Fiducial points or monuments can also be evaluated in the latter stages of the patient's cardiac cycle. For example, a fiducial point corresponding to the tail end of the RV EGM signal is indicated RVt 320 and a similar fiducial point or monument for the tail end of the LV EGM signal indicated LVt 322. A monument RV rep 324 is also defined corresponding to the end of RV repolarization. Similarly, a fiducial point or monument indicated LV rep 326 is defined corresponding to the end of LV repolarization.

It will be understood that the illustration of FIG. 4 is schematic in nature and should not to be understood to be strictly to scale or representative of any given patient's particular EGM morphology. However, these or other fiducial points or monuments can be evaluated as indicators of the relative synchrony or dysynchrony exhibited by the patient. As previously noted, indicators of dysynchrony based on EGM measures, such as one or more of the waveforms 302, 304, 306 can be utilized by a clinician with appropriate waiting factors to determine an index of dysynchrony D. Such EGM-based measures of synchrony/dysynchrony can be advantageously utilized by the clinician for modification of the patient's therapy for improved efficacy including but not limited to reprogramming of the device 10, self programming or closed-loop reprogramming of the device 10, and/or modification of an existing device 10 or replacement with another device 10 capable of CRT therapy.

Figure 5:
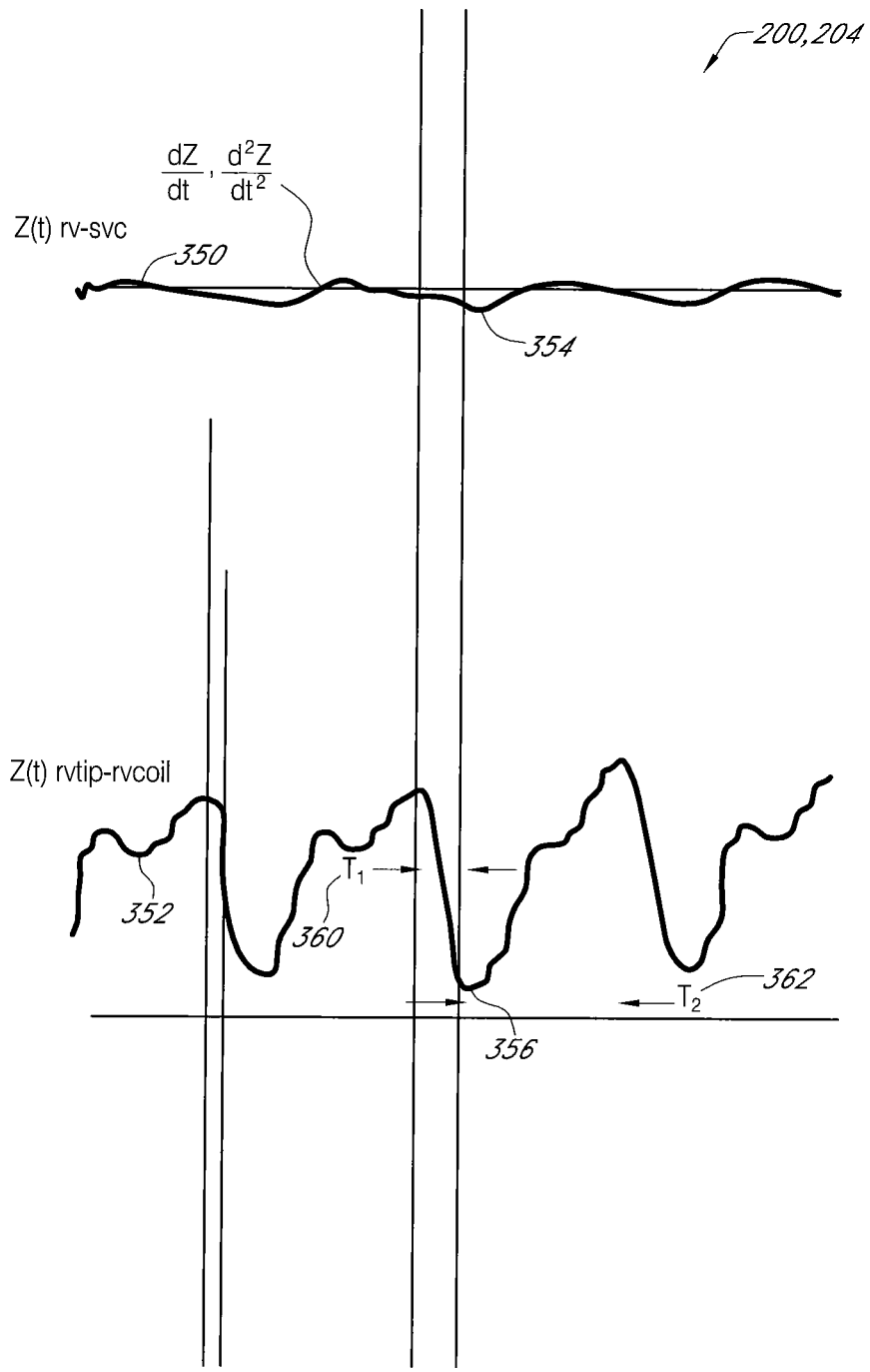
FIG. 5 illustrates exemplary impedance waveforms indicative of physiologic activity as measured along different sensing vectors.

FIG. 5 illustrates exemplary waveforms of electrical impedance indicative of changes in myocardial impedance over time as measured along different spatial vectors. As previously noted, impedance measures are indicative of contraction/relaxation of myocardium and of filling and expulsion of blood. A first impedance waveform 350 corresponds to impedance measurements made between electrodes arranged adjacent a patient's right ventricle and superior vena cava (SVC). A second impedance waveform 352 corresponds to impedance as measured between an RV tip and an RV coil electrode.

The impedance waveforms 350, 352 also define a number of representative fiducial points or monuments, such as peaks 354 and 356, and temporal intervals, e.g. T1 360 and T2 362. In some applications, use of higher frequency current stimuli to perform impedance sensing will result in current density more proximate to the electrodes being used and reduce far field noise. Variations of sampling rate, impedance current frequency, pulse width, and/or amplitude can also be evaluated for improved signal quality. Use of ensemble averaging techniques across a given or multiple vectors can also be used to achieve higher signal quality. Ensemble averaging can provide a representative "composite" waveform obtained from a plurality of separate sensing cycles. The composite waveforms or characteristics tend to be more representative of the underlying repetitive physiologic activity and tend to suppress random noise and anomalous physiologic activity.

The first and/or second derivatives of the impedance waveforms 350, 352, $dZ/dt$ and $d^2Z/dt^2$, can also provide useful data indicative of myocardial contractility. Again, multiple impedance sensing electrode pairs arranged along multiple vectors can provide insight into regional activity, such as regional myocardial activity.

As previously noted, in certain embodiments it is preferred that the capability be provided to sense impedance across a plurality of different sensing vectors to facilitate determination of regional properties. In one embodiment, right heart impedance sensing can be performed by applying current between a RA ring and RV tip electrodes with the RA tip and RV ring electrodes used for corresponding sensing. In another embodiment, current pulses can be delivered between the RV tip and can/housing electrodes and a corresponding voltage measurement made between the RV ring and RV coil electrodes to determine RV impedance curve data. Delivering current between the RV tip and SVC/can electrodes with corresponding voltage measurements being made between the RV ring and RV coil electrodes can provide more globally indicative data.

Impedance measurements can be obtained over multiple cardiac cycles and the results of each cycle can be combined by ensemble averaging techniques to generate representative impedance characteristics having improved signal to noise. Measurements taken across multiple vectors can also be combined to generate one or more "global" impedance signals. In various embodiments, measurements across multiple vectors can be performed substantially simultaneously and/or separated in time.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac therapy device comprising:
    an implantable stimulation pulse generator;
    one or more implantable leads defining sensing and stimulation circuits adapted to sense and deliver therapy in at least one right side heart chamber; and
    an implantable controller in communication with the stimulation pulse generator and the one or more leads so as to receive sensed signals indicative of a patient's physiologic activity, the controller being adapted to evaluate the patient's physiologic activity as indicated by the received sensed signals and to induce the stimulation pulse generator to deliver therapeutic stimulation via the one or more leads and wherein the controller is further adapted to monitor at least one indicator of electro-mechanical cardiac dysynchrony and to compare the at least one indicator to a determined electro-mechanical dysynchrony threshold wherein the threshold is determined for indications that the patient be further evaluated for cardiac resynchronization therapy and wherein the controller is further adapted to set an alert when the at least one indicator exceeds the threshold;
    wherein the one or more implantable leads are adapted to deliver pacing therapy to the right ventricle and wherein the controller monitors a frequency of right ventricle pacing therapy delivery and wherein the controller evaluates dysynchrony at least partially as a function of the frequency of right ventricle pacing therapy delivery.

2. The therapy device of claim 1, wherein the one or more implantable leads are adapted to develop a plurality of electrogram waveforms corresponding to electrical activity arising from the patient's cardiac activity and wherein the controller evaluates dysynchrony at least partially as a function of the electrogram waveforms.

3. The therapy device of claim 2, wherein the electrogram waveforms define a plurality of fiducial points including one or more of onsets, peaks, and ends and wherein the controller evaluates dysynchrony at least partially as a function of relative temporal occurrence of the fiducial points.

4. The therapy device of claim 3, wherein the controller evaluates dysynchrony at least partially as a function of relative temporal occurrence of corresponding fiducial points between different electrogram waveforms.

5. The therapy device of claim 1, wherein the one or more implantable leads are adapted to develop a plurality of impedance waveforms indicative of the impedance of cardiac tissue and wherein the controller evaluates dysynchrony at least partially as a function of the impedance waveforms.

6. The therapy device of claim 1, wherein the one or more implantable leads are adapted to perform two or more of developing electrogram waveforms, developing impedance waveforms, and delivering pacing therapy to the right ventricle at a monitored frequency and wherein the controller evaluates dysynchrony as a function of at least two of the electrogram waveforms, the impedance waveforms, and the right ventricular pacing frequency.

7. The therapy device of claim 1, further comprising a communication component in communication with the controller and wherein the alert is actively communicated outside the device.

* * * * *